United States Patent
Tückmantel et al.

(10) Patent No.: US 6,271,379 B1
(45) Date of Patent: Aug. 7, 2001

(54) INTERMEDIATES USEFUL FOR THE SYNTHESIS OF HUPERZINE A

(75) Inventors: Werner Tückmantel, Washington, DC (US); Alan P. Kozikowski, Princeton, NJ (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/520,497

(22) Filed: Mar. 8, 2000

(51) Int. Cl.[7] ............... C07D 221/22; C07D 213/64
(52) U.S. Cl. ................ 546/97; 546/296; 546/301; 546/303
(58) Field of Search ................ 546/97, 296, 303, 546/301

(56) References Cited

U.S. PATENT DOCUMENTS

| | | |
|---|---|---|
| 4,929,731 | 5/1990 | Kozikowski et al. . |
| 5,104,880 | 4/1992 | Kozikowski . |
| 5,106,979 | 4/1992 | Kozikowski et al. . |
| 5,547,960 | 8/1996 | Kozikowski et al. . |
| 5,663,344 | 9/1997 | Kozikowski et al. . |
| 5,869,672 | 2/1999 | Kozikowski et al. . |

FOREIGN PATENT DOCUMENTS

| | | |
|---|---|---|
| 10158289 | * 6/1998 | (JP) . |
| WO 99/11625 | 3/1999 | (WO) . |

OTHER PUBLICATIONS

Campiani et al., 1998, "Synthesis and Anticholinesterase Activity of Huperzine A Analogues Containing Phenol and Catechol Replacements for the Pyridone Ring", Bioorganic & Medicinal Chem. Lett. 8:1413–1418.

Chassaing et al., 1997, "New Straightforward Route to an Huperzine A Synthetic Intermediate", Synthetic Comm. 27:61–68.

Fanxing et al., 1998, "Synthesis and Acetylcholinesterase Inhibitory Activity of (+/−)–14–Fluorohuperzine A", Bioorganic & Medicinal Chem. Lett. 8:1661–1664.

Gravel et al., 1984, "Total Regiospecific Synthesis of the Selagine Tricyclic Ring System", Can. J. Chem. 62:2945–2947.

Kaneko et al., 1997, "Synthesis of (+/−)–12–Fluorohuperzine A, a Novel Acetylcholinesterase Inhibitor", Synlett 5:447–448.

Kozikowski et al., 1996, "Synthesis of (+/−)–10, 10–Dimethylhuperzine A—a Huperzine Analogue Possessing a Slower Enzyme Off–Rate", Bioorganic & Medicinal Chem. Lett. 6:259–262.

Kozikowski et al. 1996, "Identification of a More Potent Analogue of the Naturally Occurring Alkaloid Huperzine A. Predictive Molecular Modeling of its Interaction with AchE", J. Am. Chem. Soc. 118:11357–11362.

Kozikowski et al., 1996, "An Approach to Modified Heterocyclic Analogues of Huperzine A and Isohuperzine A. Synthesis of the Pyrimidone and Pyrazole Analogues, and their Anticholinesterase Activity", J. Chem. Soc. Perkins Trans. 1:1287–1297.

Kozikowski et al., 1995, "Synthesis and Acetylcholinesterase Activity of Several Pyrimidone Analogues of Huperzine A", J. Chem. Soc. Chem. Comm. pp. 283–285.

Liu et al. 1986, "The Structures of Huperzine A and B, Two New Alkaloids Exhibiting Marked Anticholinesterase Activity", Can. J. Chem. 64:837–839.

Saxena et al., 1998, "Characterization of C–10 Substituted Analogues of Huperzine A as Inhibitors of Cholinesterases", in: *Progress in Alzheimer's and Parkinson's Diseases*, Fisher et al., Plenum Press, New York, pp. 601–605.

Snieckus, 1990, "Directed Ortho Methylation. Tertiary Amide and o–Carbamate Directions in Synthetic Strategies for Polysubstituted Aromatics", Chem. Rev. 90:879–933.

Foricher et al., 2000, "A Convergent Approach to Huperzine A and Analogues" Tetrahedron Lett. 41:2007–2009.

* cited by examiner

*Primary Examiner*—Evelyn Mei Huang
(74) *Attorney, Agent, or Firm*—Pennie & Edmonds LLP

(57) ABSTRACT

Intermediates useful for the synthesis of huperzine A represented by the structures below,

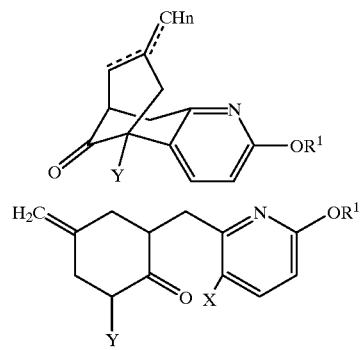

and methods for their synthesis, wherein:

$R^1$ is lower alkyl, benzyl, or substituted benzyl;

X is a suitable leaving group;

Y is an electron withdrawing group that can subsequently be converted into an amino group;

one broken line is present as a carbon—carbon bond and the other broken line is absent, where the broken line forms an unconjugated carbon—carbon double bond, which double bond may be endocyclic whereby n is 3 or the double bond may be exocyclic whereby n is 2.

12 Claims, No Drawings

INTERMEDIATES USEFUL FOR THE SYNTHESIS OF HUPERZINE A

FIELD OF INVENTION

The present invention relates to huperzine A, methods for the synthesis of huperzine A, and intermediates useful for the synthesis of huperzine A.

BACKGROUND OF THE INVENTION

Approximately 5–15% of the population of the United States over age 65 (1.24 million) has Alzheimer's disease. This disease is the most frequent cause of institutionalization for long-term care. In 1983, more than $27 billion was spent in the U.S. in health care for Alzheimer's afflicted individuals.

Six basic research areas of Alzheimer's have been defined by R. J. Wurtman, *Scientific Amer.*, 62 (1985). These areas include faulty genes, accumulations of amyloid protein, infectious agents, environmental toxins (e g., aluminum and certain unusual amino acids), inadequate blood flow and energy metabolism, and cholinergic deficits.

A number of possible therapeutic interventions are currently under study. These include the use of nerve growth factors (NGF), muscarinic and nicotinic agonists, acetylcholinesterase (AChE) inhibitors, GABA-inverse agonists, NMDA modulators, and others. It is, however, unlikely that any single drug will restore cognition, especially in view of the involvement of a number of different neurotransmitter systems in memory processing.

While it is known that defects in neurotransmitter systems other than cholinergic systems play a role in the memory loss associated with Alzheimer's disease, findings by K. L. Davis, presented at "New Strategies for the Treatment of Alzheimer's Disease," NIA Meeting (Jan. 8–10, 1990) indicated that administration of AChE inhibitors, such as physostigmine, result in modest cognitive improvement and may prove useful for treating Alzheimer's disease when administered in combination with other drugs such as clonidine, deprenyl or desipramine.

To the extent ACHE inhibitors can serve as useful adjuncts in the treatment of Alzheimer's disease, two relatively new lycopodium alkaloids, (–)-huperzine A and B, isolated from *Huperzia serrata* (Thunb.) Trev., a Chinese folk medicine, appear superior to THA and physostigmine (U.S. Pat. No. 5,177,082 to Yu et al.; J. S. Liu et al., *Can. J. Chem.*, 64, 837 (1986); W. A. Ayer et al., ibid., 67, 1077 (1989), ibid., 67, 1538 (1989)). The structure of (–)-huperzine A (1) is depicted below:

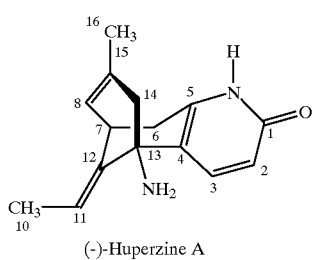

(-)-Huperzine A

In studies performed in China, these compounds have been found to improve memory and learning in animals (X. C. Tang et al., *Acta Pharmacol Sin.*, 7, 507 (1986)). Additionally, workers at Hoffman LaRoche studied (–)-huperzine A in mice and squirrel monkeys and found it to be an effective cognition enhancer (G. P. Vincent et al., *Neurosci. Abst.*, 13, 884 (1987)). The duration of action of a single dose (2 mg/kg i.m.) of (–)-huperzine A is over 6 hr, a remarkable result in relation to the AChE inhibitory action of physostigmine (0.65 mg/kg i.m.), which has a maximal duration of action of 60 min and which causes considerable side effects (X. C. Tang et al., *J. Neurosci. Res.*, 24, 276 (1989)). (–)-Huperzine A has been further tested in 128 patients suffering from myasthenia gravis and found to control the clinical manifestations of the disease in 99% of these cases (Y. S. Cheng, *New Drugs and Clinical Remedies*, 5, 197 (1986)).

Other pharmacological agents that circulate systemically but that are targeted to brain tissue have enjoyed only limited success. For such pharmacological agents to enter brain tissue in therapeutically effective concentrations, the blood-brain barrier, a network of tightly joined endothelial cells of central nervous system capillaries, must first be penetrated. Because the membranes of the endothelial cells are phospholipoidal in nature, pharmacological agents that are lipophilic in nature are better able to diffuse through the blood-brain barrier than those that are not (see Marcus E. Brewster et al., *Chemical Approaches to Brain-Targeting of Biologically Active Compounds*, in *Drug Design for Neuroscience* 435–67 (Alan P. Kozikowski ed., Raven Press, Ltd. 1993).

While huperzine A is a promising candidate for treatment of Alzheimer's disease, extraction of practical quantities from its natural source is difficult. Furthermore, only a limited number of huperzine A synthetic procedures have been disclosed, which are, for the most part, complicated and non-convergent, e.g., Kaneko et al., *Tetrahedron, Asymmetry* 8, 829–832 (1997); Chassaing el al., *Synth. Conmnun.* 27, 61–68 (1997); Kaneko et al., *Tetrahedron* 54, 5485–5506 (1998); Qian et al., *Tetrahdron Leti.* 30, 2089–2090 (1989)).

Accordingly, there remains a need for convergent synthetic methods toward huperzine A and precursors therefor.

SUMMARY OF THE INVENTION

The present invention relates to intermediates, having a structure represented by formula 2 below, that can be converted into huperzine A

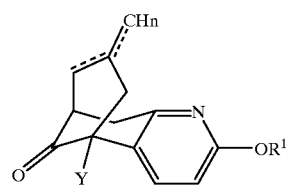

wherein:

$R^1$ is lower alkyl, benzyl, or substituted benzyl;

Y is selected from the group consisting of —$NO_2$, —$NHR^2$, —$NR^3R^4$, —CH=$NOR^5$, —$COR^6$, —COCl, —$CO_2R^6$, —C(O)$NR^6R^7$, —CN, —C(S)$NR^6R^7$, —$N_3$, —$SR^6$, and —N=$CR^8R^9$;

$R^2$ is an amino protecting group;

$R^3$ and $R^4$ are independently selected from the group consisting of —C(O)$OR^{10}$, —C(O)$R^{10}$, allyl, benzyl, substituted benzyl, phenacyl, and 3-acetoxypropyl or $R^3$ and $R^4$ may be taken together to form a cyclic imide;

$R^5$ is selected from the group consisting of hydrogen, lower alkyl, and aryl;

$R^6$ and $R^7$ are independently selected from the group consisting of hydrogen, lower alkyl, substituted lower alkyl, aryl, and substituted aryl or $R^6$ and $R^7$ may be taken together to form a heterocyclic ring;

$R^8$ and $R^9$ are independently selected from the group consisting of hydrogen, lower alkyl, substituted lower alkyl, aryl, and substituted aryl or $R^8$ and $R^9$ may be taken together to form a ring;

$R^{10}$ is selected from the group consisting of lower alkyl, substituted lower alkyl, aryl, substituted aryl, adamantyl, cinnamyl, 2-trimethylsilylethyl, 2-phenylethyl, vinyl, allyl, benzyl, and substituted benzyl; and one broken line is present as a carbon—carbon bond and the other broken line is absent, where the broken line completes an unconjugated carbon—carbon double bond, which double bond may be endocyclic whereby n is 3 or the double bond may be exocyclic whereby n is 2.

The invention also relates to methods for the synthesis of a compounds of formula 2, and methods for conversion of a compound of formula 2 into huperzine A.

In another embodiment, the invention relates to compounds of formula 3 shown below:

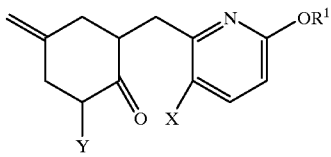

3 wherein:

$R^1$ is lower alkyl, benzyl, or substituted benzyl;

X is a suitable leaving group;

Y is selected from the group consisting of hydrogen, $-NO_2$, $-NR^3R^4$, $-CH=NOR^5$, $-COR^6$, $-CO_2R^6$, $-C(O)NR^6R^7$, $-CN$, $-C(S)NR^6R^7$, $-N_3$, and $-N=CR^8R^9$;

$R^3$ and $R^4$ are independently selected from the group consisting of $-C(O)OR^{10}$, $-C(O)R^{10}$, phenacyl, and 3-acetoxypropyl or $R^3$ and $R^4$ may be taken together to form a cyclic imide;

$R^5$ is selected from the group consisting of hydrogen, lower alkyl, and aryl;

$R^6$ and $R^7$ are independently selected from the group consisting of hydrogen, lower alkyl, substituted lower alkyl, aryl, and substituted aryl or $R^6$ and $R^7$ may be taken together to form a heterocyclic ring;

$R^8$ and $R^9$ are independently selected from the group consisting of hydrogen, lower alkyl, substituted lower alkyl, aryl, and substituted aryl or $R^8$ and $R^9$ may be taken together to form a ring; and $R^{10}$ is selected from the group consisting of lower alkyl, substituted lower alkyl, aryl, substituted aryl, adamantyl, cinnamyl, 2-trimethylsilylethyl, 2-phenylethyl, vinyl, allyl, benzyl, and substituted benzyl.

The invention also relates to methods for the synthesis of a compound of formula 3, and methods for conversion of a compound of formula 3 into a compound of formula 2.

The present invention can be understood more fully by reference to the following detailed description and illustrative examples that are intended to exemplify non-limiting embodiments of the invention.

DESCRIPTION OF THE INVENTION

As used in the present application, the following definitions apply:

A "suitable substituent" is intended to mean one or two chemically acceptable functional groups, i.e., one or two moieties that do not negate the synthetic utility of the inventive compounds. Such suitable substituents may be routinely selected by those skilled in the art. Illustrative examples of suitable substituents include, but are not limited to alkyl, aryl, heteroaryl, cycloalkyl, heterocycloalkyl, halo, $-CN$, $-OH$, oxo, $-SH$, $-S-$alkyl, $-S-$aryl, $-O-$alkyl, $-O-$aryl, $-CO_2H$, $-NH_2$, $-NH$(alkyl), $N(alkyl)_2$, $-NH$(aryl), $-N(aryl)_2$, $CO$(alkyl), $-CO_2$(alkyl), $-CO$(aryl), $-CO_2$(aryl), $-SO_2$(alkyl), $-SO_2$(aryl), $-C(O)NH_2$, $-C(O)NH$(alkyl), $C(O)N(alkyl)_2$, $C(O)NH$(aryl), $C(O)N(aryl)_2$, $-C(S)NH_2$, $-C(S)NH$(alkyl), $C(S)N(alkyl)_2$, $C(S)NH$(aryl), $C(S)N(aryl)_2$ and the like. According to the present invention, when a group is substituted it is considered substituted with one or more suitable substituents as defined above.

When any of the R groups discussed herein is substituted (e.g., substituted benzyl, substituted alkyl, or substituted aryl) the identity of the substituent is generally not important. Substituents are merely required not to negate the synthetic utility of the compounds of the invention and, preferably, will be chosen by the skilled artisan to enhance the synthetic processes described herein. For example, a substituent may be one or more of any of the suitable substituent listed above. More preferred substituents include nitro, methoxy, dimethoxy, hydroxy, halo, dihalo, trihalo, and alkyl.

An "oxo group" is intended to mean the radical $=O$.

A "protected amino-group" means a functional group unreactive to the conditions of a particular reaction step(s) that may subsequently be selectively converted to an amino group. For example the radical $-NHR^2$ wherein $R^2$ is an amino protecting-group.

An "amino-protecting group" means any group that is reversibly attached to an amino-group, that renders the amino-group unreactive during a subsequent reaction(s) and that can be selectively cleaved to regenerate the amino function once its protecting purpose has been served. Examples of amino-protecting groups are found in Greene, T. W., *Protective Groups in Organic Synthesis,* 3rd edition 504–573 (1999), incorporated herein by reference. Examples of suitable amino protecting groups suitable for use with the invention include but are not limited to $-C(O)OR^{10}$, $-C(O)R^{10}$, allyl, phenacyl, 3-acetoxypropyl, wherein $R^{10}$ includes such groups as lower alkyl (e.g., methyl, ethyl, t-butyl), substituted lower alkyl (e.g., haloalkyl), aryl, substituted aryl, adamantyl, cinnamyl, 2-trimethylsilylethyl, 2-phenylethyl, vinyl, allyl, benzyl, or substituted benzyl.

Preferably, the amino function of the present invention, is protected as a carbamate group (i.e. $-NHC(O)OR^{10}$, Greene, T. W., *Protective Groups in Organic Synthesis* 503–510 (1999)) and Corey et al., *Tetrahedron Lett.,* 1051 (1978); both of which are incorporated herein by reference). The preferred carbamate, in the present invention is the N-tert-butyloxycarbonyl (N-BOC) group, Carpino, L. A. *Acc. Chem. Res.* 6, 191 (1973), incorporated herein by reference.

As used herein the term "halogen" means fluoro, chloro, bromo, or iodo.

An "alkyl group" is intended to mean a straight or branched chain monovalent radical of carbon and hydrogen atoms and having no unsaturation, which may be unsubstituted or substituted by one or more suitable substituents.

A "lower alkyl group" is intended to mean an alkyl group as defined above which has from 1 to 8 carbon atoms, such as methyl, ethyl, t-butyl, or propyl, which may be unsubstituted or substituted by one or more suitable substituents. Preferred lower alkyl groups include methyl and t-butyl.

An "alkylene group" is intended to mean a straight or branched-chain divalent radical of carbon and hydrogen atoms and having no unsaturation, such as methylene, ethylene, propylene and the like, which may be substituted by one or more suitable substituents.

An "aryl group" is intended to mean a mono- or polycyclic aromatic radical containing carbon atoms. The aromatic ring (or rings when the aryl group is polycyclic), preferably, comprise 6 ring carbon atoms, which rings may be unsubstituted or substituted by one or more suitable substituents as defined above. Exemplary aryl groups include but are not limited to phenyl, tolyl, xylyl, hydroxyphenyl and α- and β-naphthyl.

A "heteroaryl group" is intended to mean a monocyclic aromatic ring containing carbon atoms, preferably 3, 4, or 5 ring carbon atoms, and one or more heteroatoms selected from nitrogen, oxygen, and sulfur, which ring may be unsubstituted or substituted by one or more suitable substituents. Illustrative examples of unsubstituted heteroaryl groups include, but are not limited to furyl, pyrrolyl, imidazolyl, pyridyl, pyrazyl, pyrazolyl, pyrimidyl, thiophenyl, and phienyl.

A "cycloalkyl group" is intended to mean a monocyclic radical containing carbon atoms, preferably 5 or 6 ring carbon atoms, and having no unsaturation, which may be unsubstituted or substituted by one or more suitable substituents.

A "heterocycloalkyl group" is intended to mean a monocyclic radical containing carbon atoms, preferably 4 to 6 ring carbon atoms, and at least one heteroatom selected from nitrogen, oxygen, and sulfur, and having no unsaturation, which may be unsubstituted or substituted by one or more suitable substituents. Examples of unsubstituted heterocycloalkyl groups include pyrrolidenyl, piperidinyl, piperazinyl, morpholinyl, and pyranyl.

Methodology and reaction procedures for the synthesis of the invention's novel intermediates, are disclosed in the following reaction schemes and examples. The procedures and methods described herein are well known to those of ordinary skill in the art. The reactions will generally take place in the presence of an organic solvent. Exemplary solvents include, but are not limited to, dichloromethane, chloroform, diethyl ether, tetrahydrofuran, dimethylformamide, benzene, toluene, saturated hydrocarbons (e.g., pentane, hexane, and heptane) and the like. Generally, the organic solvent comprises about 95 to about 30 weight percent of the total reaction mixture.

As used herein the term, "reagent" is meant to encompass any of the chemicals described herein, i.e., all the reactants, intermediates, bases, acids, catalysts, and solvents.

The term "workup" is defined as the sequence of steps performed on a reaction mixture to obtain the reaction product in crude form prior to purification. A general workup procedure may involve quenching the reaction mixture; diluting the reaction mixture with a water insoluble organic solvent; adding an aqueous phase to wash the organic phase; separating, drying, and concentrating the organic phase to a crude residue. Concentration of the organic phase comprises removal of volatiles such as solvents. Concentration is usually effected under vacuum (about 5 mmHg to about 100 mmHg), e.g., on a roto-evaporation apparatus. The crude residue comprises the desired compound and any other by-products.

As used herein the term "quenching" means deactivating the reaction mixture's active components after the reaction is complete. Typically, quenching a reaction mixture involves adding water, an aqueous buffer, an aqueous acid, or an aqueous base at about room temperature to about 0° C. and agitating the mixture. Quenching procedures are well known to those of ordinary skill in the art and readily selected according to the reaction.

Optionally, before concentrating the washed and dried organic phase, an adsorbent such as CELITE® or silica gel can be added, and the resulting suspension concentrated such that the crude concentrated residue is adsorbed onto the surface of the adsorbent. The adsorbent/compound can then be added directly to a silica gel-filled column for purification.

There are many variations of this general workup procedure and one of ordinary skill in the art can readily select the appropriate workup conditions depending of the type of reaction and the product identity.

The reactions described herein are generally performed by combining the reagents in a specified manner, usually in the presence of an organic solvent; allowing the reagents to react for the appropriate time at the appropriate temperature; and monitoring the reaction progress by an appropriate analytical method. Analytical methods include but are not limited to visual inspection, thin layer chromatography, NMR spectroscopy, gas chromatography, liquid chromatography, UV spectroscopy, and infrared spectroscopy.

One of ordinary skill in the art is readily capable of optimizing the reaction conditions and selecting the appropriate analytical method. When the reaction is substantially complete, the desired compound can be isolated by workup and subsequently purified via recrystallization, distillation, steam distillation, preparative thin layer chromatography, column chromatography including flash chromatography and high performance liquid chromatography, or other means well known to those skilled in the art.

In one embodiment, the present invention provides intermediates represented by formula 2 below that are readily transformed into huperzine A:

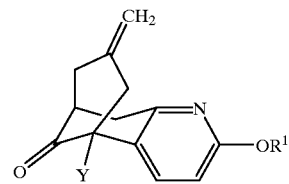

2 wherein:

$R^1$ is lower alkyl, benzyl, or substituted benzyl;

Y is selected from the group consisting of $-NO_2$, $-NHR^2$, $-NR^3R^4$, $-CH=NOR^5$, $-COR^6$, $-COCl$, $-CO_2R^6$, $-C(O)NR^6R^7$, $-CN$, $-C(S)NR^6R^7$, $-N_3$, $-SR^6$, and $-N=CR^8R^9$;

$R^2$ is an amino protecting group;

$R^2$ may be any amino-protecting group as defined above. Examples of suitable $R^2$ groups include but are not limited to $-C(O)OR^{10}$, $-C(O)R^{10}$, allyl, benzyl, substituted benzyl, alkyl, substituted lower alkyl, phenacyl, and 3-acetoxypropyl;

$R^3$ and $R^4$ are independently selected from the group consisting of hydrogen, $-C(O)OR^{10}$, $-C(O)R^{10}$, allyl, benzyl, substituted benzyl, phenacyl, and 3-acetoxypropyl, or $R^3$ and $R^4$ may be taken together to form a cyclic imide;

$R^5$ is selected from the group consisting of hydrogen, lower alkyl, and aryl;

$R^6$ and $R^7$ are independently selected from the group consisting of hydrogen, lower alkyl, substituted alkyl (e.g., haloalkyl), aryl, and substitute aryl (e.g., haloaryl) or $R^6$ and $R^7$ may be taken together to form a heterocyclic ring.

Preferably, $R^8$ and $R^9$ are independently selected from the group consisting of hydrogen, lower alkyl, aryl, substituted lower alkyl, and substituted aryl or $R^8$ and $R^9$ may be taken together to form a ring.

Preferred $R^{10}$ groups include but are not limited to lower alkyl, substituted lower alkyl, haloalkyl, aryl, substituted aryl, adamantyl, cinnamyl, 2-trimethylsilylethyl, 2-phenylethyl, vinyl, allyl, benzyl, and substituted benzyl.

Preferably Y is selected from the group consisting of —$NO_2$, —CHO, —$NH_2$, —$NHR^2$, —C(O)$NH_2$, —CH=NOH, —CN, —C(S)$NH_2$, —COCl, and —$N_3$, more preferably Y is —$NO_2$.

When $R^3$ and $R^4$ are taken together to form a cyclic imide, the imide may be any of those listed in Greene, T. W., *Protective Groups in Organic Synthesis*, 3rd edition 564–573 (1999). Examples include, but are not limited to, N-phthalimide, substituted N-phthalimides (e.g., N-halophthalimide, N-nitrophthalimide), N-succinimide, and substituted N-succinimides (e.g., N-dithiasuccinimide).

In another embodiment, shown in Scheme I below, the invention provides intermediates of formula 5, wherein Y and $R^1$ have the meanings as defined above. As shown below, a compound of formula 5 wherein the double bond is in the endocyclic position can be prepared from a compound of formula 2 (where the double bond is exocyclic) by simple double bond rearrangement.

SCHEME I

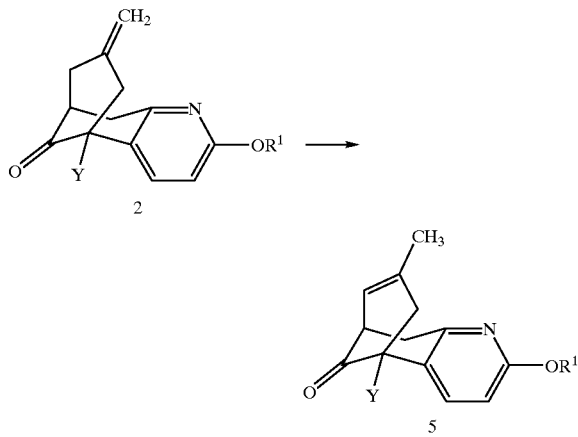

This rearrangement can be accomplished by treatment with an acid in an organic solvent. For example, heating with trifluoromethansulfonic acid in dry dioxane (Kozikowski et al., *J. Chem. Soc., Perkin Trans.* 1, 1287–1297, 1995).

In a further embodiment of the invention, a compound of formula 2 can be prepared via cyclization of a compound of formula 3 as outlined in Scheme II below, where $R^1$ is defined as above, X is a suitable leaving groups, and Y is a suitable electron withdrawing group that may, during a subsequent synthetic step(s), be converted into an amino-group.

SCHEME II

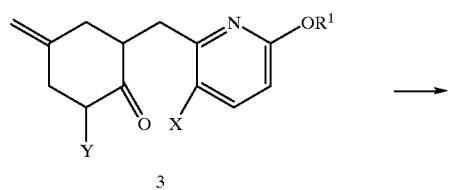

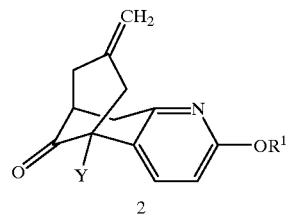

An electron withdrawing group, as is well known in the art, is a radical that withdraws electron density from adjacent atoms and, as such, will increases the acidity of hydrogen atoms on adjacent carbon atoms (i.e., α-hydrogens). In the present invention, preferred electron withdrawing groups are those that will increase the acidity of an α-hydrogen on an unsaturated alkyl group such that the $pK_a$ value is within the range of about 37 to about 5. The $pK_a$ is a measure of acid strength of an acid HA according to the equation $pK_a = -\log K_a$ wherein $K_a = [H_3O^+][A^-]/HA$. For tables of $pK_a$ values for substituent groups and a discussion see March, J. *Advanced Organic Chemistry; Reactions Mechanisms, and Structure*, 4th ed., 1992, p. 248–272; incorporated herein by reference. According to the invention, the electron withdrawing group will be chosen such that it may be converted into an amino group and is inert under the reaction conditions required to convert of formula 3 into give a compound of formula 2. These groups and synthetic methods for their conversion into an amino group may be chosen from among those well known in the art, e.g., see March, J. *Advanced Organic Chemistry; Reactions Mechanisms, and Structure*, 4th ed., 1992, p. 1276–1277, incorporated herein by reference.

Suitable electron withdrawing groups that may subsequently be converted into an amino group include but are not limited to —$NO_2$, —$NR^3R^4$, —CH=$NOR^5$, —$COR^6$, —$CO_2R^6$, —C(O)$NR^6R^7$, —CN, —C(S)$NR^6R^7$, —$N_3$, and —N=$CR^8R^9$, wherein:

$R^3$ and $R^4$ are independently selected from the group consisting of
—C(O)$OR^{10}$, —C(O)$R^{10}$, phenacyl, and 3-acetoxypropyl or $R^3$ and $R^4$ may be taken together to form a cyclic imide;

$R^5$ is selected from the group consisting of hydrogen, alkyl, and aryl;

$R^6$ and $R^7$ are independently selected from the group consisting of hydrogen, alkyl, substituted lower alkyl, aryl, and substituted aryl or $R^6$ and $R^7$ may be taken together to form a heterocyclic ring;

$R^8$ and $R^9$ are independently selected from the group consisting of hydrogen, lower alkyl, substituted lower alkyl, aryl, and substituted aryl or $R^8$ and $R^9$ may be taken together to form a ring;

$R^{10}$ is selected from the group consisting of lower alkyl, substituted lower alkyl, aryl, substituted aryl, adamantyl, cinnamyl, 2-trimethylsilylethyl, 2-phenylethyl, vinyl, allyl, benzyl, and substituted benzyl.

X can be any suitable leaving group, examples include but are not limited to iodo; bromo; chloro; aryl- or alkylsulfonyloxy, substituted arylsulfonyloxy (e.g., tosyloxy or mesyloxy); substituted alkylsulfonyloxy (e.g., haloalkylsulfonyloxy); phenoxy or subsituted phenoxy; and acyloxy groups.

The cyclization can be accomplished by methods well known in the art. One method is the well known SNAr type reaction (e.g., see Bernasconi *Acc. Chem Res.* 11, 147–152

(1978), incorporated by reference herein). This involves treatment of 3 with a strong base, such as sodium amide (Leake et al., *J. Am. Chem. Soc.* 81, 1169, 1627(1959)) or lithium diisopropylamide Caubere et al., *Bull. Soc. Chim. Fr.* 4643, 4649 (1972) both of which citations are incorporated herein by reference).

Another method for cyclization of a compound of formula 3 is an SRN1 type reaction. This type of cyclization, as well known to those of skill in the art, can be initiated photochemically (e.g., see Cornelisse et al., *Adv. Phys. Org. Chem.* 11, 225–266(1975)) electrochemically (e.g., see Saveant et al., *Acc. Chem. Res.* 13, 323–329 (1980) and Alam et al., *J. Org. Chem.* 55, 6347(1990)) or thermally (e.g., see Swartz et al., *J. Org. Chem.* 44, 340 (1979)) all of which references are incorporated herein by reference.

Ring closure of a compound of formula 3 may also be accomplished with copper halide or palladium catalysts, via the well known Hurtley reaction (e.g., Bruggink et al., *Tetrahedron* 31, 2607 (1975); McKillop *Synthesis* 759 (1977); Setsune et al., *Chem. Lett.* 367 (1981); Osuka et al., *Synthesis* 67 (1983); Uno et al., *Synthesis* 506 (1985), all of which references are incorporated herein by reference). For example, a suspension of base (1–2 equivalents), preferably potassium t-butoxide in an organic solvent, preferably monoglyme (about 20 to about 50 equivalents) is added portion-wise to a stirred solution of 3 in an organic solvent, preferably monoglyme (about 20 to about 50 equivalents) and a palladium catalyst, preferably, dichloro-bis-[triphenylphosphine]palladium (about 0.1 to about 0.5 equivalents, preferably about 0.4 equivalents), under an inert atmosphere at a temperature of about 0° C. to about 70° C., preferably at about room temperature. The resulting mixture is heated, preferably from about 40° C. to about reflux, preferably at about 70° C. for about 30 minutes to about 10 hours, preferably for about 5 hours. The progress is monitored by a suitable analytical technique and, when substantially complete, the reaction is quenched and the product isolated and purified according to standard procedures.

In another embodiment of the invention, a compound of formula 3 can be prepared by doubly-deprotonating a compound of formula 16 with 2 equivalents of a strong base then adding a compound of formula 18 (see Scheme III below). $R^1$ is defined as above, X and L are suitable leaving groups, and Y is a suitable electron withdrawing group that may, during a subsequent synthetic step(s), be converted into an amino-group, as defined above. Examples of suitable bases include but are not limited to alkyllithium amides, such as lithium tetramethylpiperidide or lithium diisopropylamide; hydride bases such as sodium or potassium hydride; alkyl-lithium bases, such as butyllithium. Preferably, the base is first added to a solution of a compound of formula 16, whereafter a solution of a compound of formula 18 is added.

SCHEME III

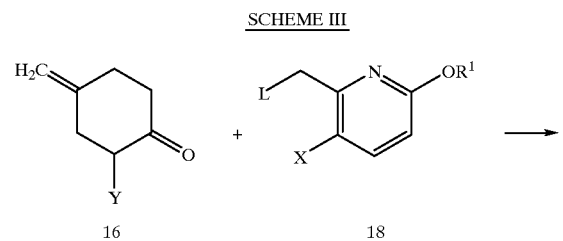

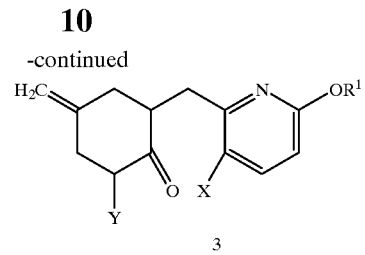

According to the invention, the electron withdrawing group will be chosen such that it may be converted into an amino group and is inert under the reaction conditions required to condense a compound of formula 16 with a compound of formula 18 to give a compound of formula 2. These groups and synthetic methods for their conversion into an amino group may be chosen from among those well known in the art, e.g., see March, J. *Advanced Organic Chemistry, Reactions Mechanisms, and Structure*, 4th ed., 1992, p. 1276–1277, incorporated herein by reference.

Suitable electron withdrawing, groups that may subsequently be converted into an amino group include but are not limited to —$NO_2$, —$NR^3R^4$, —CH=$NOR^5$, —$COR^6$, —$CO_2R^6$, —C(O)$NR^6R^7$, —CN, —C(S)$NR^6R^7$, and —N=$CR^8R^9$, wherein:

$R^3$ and $R^4$ are independently selected from the group consisting of —C(O)$OR^{10}$, —C(O)$R^{10}$, phenacyl, and 3-acetoxypropyl or $R^3$ and $R^4$ may be taken together to form a cyclic imide;

$R^5$ is selected from the group consisting of hydrogen, alkyl, and aryl;

$R^6$ and $R^7$ are independently selected from the group consisting of hydrogen, alkyl, substituted lower alkyl, aryl, and substituted aryl or $R^6$ and $R^7$ may be taken together to form a heterocyclic ring;

$R^8$ and $R^9$ are independently selected from the group consisting of hydrogen, lower alkyl, substituted lower alkyl, aryl, and substituted aryl or $R^8$ and $R^9$ may be taken together to form a ring;

$R^{10}$ is selected from the group consisting of lower alkyl, substituted lower alkyl, aryl, substituted aryl, adamantyl, cinnamyl, 2-trimethylsilylethyl, 2-phenylethyl, vinyl, allyl, benzyl, and substituted benzyl.

X and L can independently be any suitable leaving group, examples include but are not limited to iodo; bromo; chloro; aryl- or alkylsulfonyloxy, substituted arylsulfonyloxy (e.g., tosyloxy or mesyloxy); substituted alkylsulfonyloxy (e.g., haloalkylsulfonyloxy); phenoxy or subsituted phenoxy; and acyloxy groups. Preferably L is a sulfonyloxy group, more preferably toluenesulfonyloxy (tosyloxy) and preferably, X is iodo.

For example a compound of formula 16 can be condensed with a compound of formula 18 to give a compound of formula 3 according to the following procedure. Hexamethylphosphoramide (about 4 to about 5 equivalents) may be added to a cooled (about −20° C. to about −40° C.) stirred mixture of a metal dialkylamide base (about 1.5 to about 2.5 equivalents), preferably lithium diisopropylamide in an organic solvent (about 20 to about 30 equivalents), preferably tetrahydrofuran, under an inert atmosphere. After a period of about 15 minutes the mixture is cooled to a temperature of about −90° C. to about 0° C. and about 1 equivalent of a compound of formula 16 is added portion-wise and the resulting mixture is stirred for about 15 minutes to about 5 hours. A compound of formula 18 (about 0.3 to about 3 equivalents) is then added portion-wise and the resulting mixture warmed to a temperature of about 0° C. to about room temperature and stirred for about 1 hour to about 6 hours. The reaction progress is followed by an appropriate analytical technique, e.g., TLC or HPLC and upon substantial completion, a compound of formula 3 is isolated and purified using standard procedures. One of skill in the art can readily adjust the reaction parameters (addition temperatures, addition times, reaction times, etc.) depending on the identity of the particular base, solvent, and activators.

In another embodiment, a compound of formula 2 can be prepared directly (as shown in Scheme IV below) by condensing a compound of formula 16 with a compound of formula 18, wherein $R^1$, X, L, and Y are as defined above.

SCHEME IV

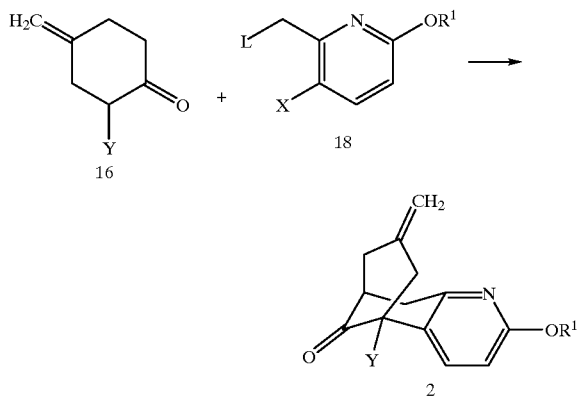

Suitable electron withdrawing groups that may subsequently be converted into an amino group include but are not limited to —$NO_2$, —$NR^3R^4$, —CH=$NOR^5$, —$COR^6$, —$CO_2R^6$, —C(O)$NR^6R^7$, —CN, —C(S)$NR^6R^7$, —$N_3$, and —N=$CR^8R^9$, wherein:

$R^3$ and $R^4$ are independently selected from the group consisting of —C(O)$OR^{10}$, —C(O)$R^{10}$, phenacyl, and 3-acetoxypropyl or $R^3$ and $R^4$ may be taken together to form a cyclic imide;

$R^5$ is selected from the group consisting of hydrogen, alkyl, and aryl;

$R^6$ and $R^7$ are independently selected from the group consisting of hydrogen, alkyl, substituted lower alkyl, aryl, and substituted aryl or $R^6$ and $R^7$ may be taken together to form a heterocyclic ring;

$R^8$ and $R^9$ are independently selected from the group consisting of hydrogen, lower alkyl, substituted lower alkyl, aryl, and substituted aryl or $R^8$ and $R^9$ may be taken together to form a ring;

$R^{10}$ is selected from the group consisting of lower alkyl, substituted lower alkyl, aryl, substituted aryl, adamantyl, cinnamyl, 2-trimethylsilylethyl, 2-phenylethyl, vinyl, allyl, benzyl, and substituted benzyl.

X and L can independently be any suitable leaving group, examples include but are not limited to iodo; bromo; chloro; aryl- or alkylsulfonyloxy, substituted arylsulfonyloxy (e.g., tosyloxy or mesyloxy); substituted alkylsulfonyloxy (e.g., haloalkylsulfonyloxy); phenoxy or subsituted phenoxy; and acyloxy groups. Preferably L is a sulfonyloxy group, more preferably toluenesulfonyloxy (tosyloxy) and preferably, X is iodo.

One of ordinary skill can condense a compound of formula 16 with a compound of formula 18 in a variety of ways. For example, R. Ballini el. al. *Synlett* 64–66 (1992), incorporated by reference herein, discloses an exemplary procedure for condensation of a compound of formula 16 with a compound of formula 18. Preferably, at least three equivalents of base are used in this transformation. Without wishing to be bound by any theory, it is believed that two equivalents of base are needed to doubly deprotonate 16, while a third equivalent is necessary to induce aryne formation by elimination of H-X from 18.

Since the aryl group of a compound of formula 18 is somewhat activated by the ring nitrogen, aryne formation may be favored (see March, J. *Advanced Organic Chemistry; Reactions Mechanisms, and Structure,* 4th ed., 1992, p. 662–664; incorporated herein by reference). This type of reaction has been used for aryne mediated ring closure (e.g., see Bunnett et al., *J. Am. Chem. Soc.* 83, 1691 (1961), incorporated herein be reference).

The suitability of the base with depend somewhat on the identity of Y and one of skill in the art may readily choose from a pool of available bases. Preferably, a strong organometallic base is used, preferably with a $pK_a$ greater than about 30. Examples include but are not limited to N-substituted lithium amides, such as lithium tetramethylpiperidide or lithium diisopropylamide; hydride bases such as sodium or potassium hydride; alkyllithium bases, such as butyllithium. Of course, if desired, the organometallic base may be activated with a complexing agent, such as N,N,N', N'-tetramethylethylenediamine (*J. Am. Chem. Soc.* 92, 4664 (1970), incorporated herein by reference) or hexamethylphosphoramide.

In the preferred procedure, an organic solution of a compound of formula 16 is added to a solution comprising about 3 equivalents of a strong base and a base activating agent. Then, to the resulting mixture, is added a compound of formula 18.

For example, hexamethylphosphoramide (about 4 to about 5 equivalents) may be added to a cooled (about −20° C. to about −40° C.) stirred mixture of a metal dialkylamide base (about 3 equivalents to about 4 equivalents), preferably lithium tetramethylpiperidide in an organic solvent (about 20 to about 30 equivalents), preferably tetrahydrofuran, under an inert atmosphere. After a period of about 15 minutes the mixture is cooled to a temperature of about −90° C. to about 0° C. and about 1 equivalent of a compound of formula 16 is added portion-wise and the resulting mixture is stirred for about 15 minutes to about 5 hours. A compound of formula 18 (about 0.3 to about 3 equivalents) is then added portion-wise and the resulting mixture warmed to a temperature of about 0° C. to about room temperature and stirred for about 1 hour to about 6 hours. The reaction progress is followed by an appropriate analytical technique, e.g., TLC or HPLC and upon substantial completion, the product is isolated and purified using standard procedures. One of skill in the art can readily adjust the reaction parameters (addition temperatures, addition times, reaction times, etc.) depending on the identity of the particular base, solvent, and activators.

A compound of formula 18 may be prepared from a compound of formula 22, wherein $R^1$ is as defined above, as shown in Scheme V, below. In the first step, treatment of a compound of formula 22 with two equivalents of an organometallic base, such as an alkyllithium, a lithiumdialkylamide, or an alkali metal bis(trimethylsilyl) amide affords intermediate dianion of formula 24. The resulting dianion is quenched with two equivalents of an electrophile to establish X and L.

SCHEME V

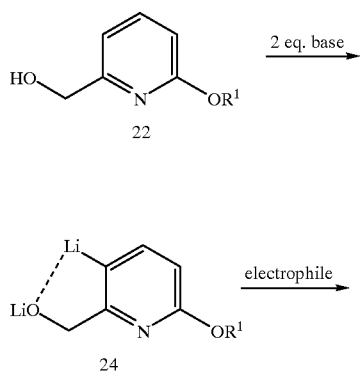

SCHEME VI

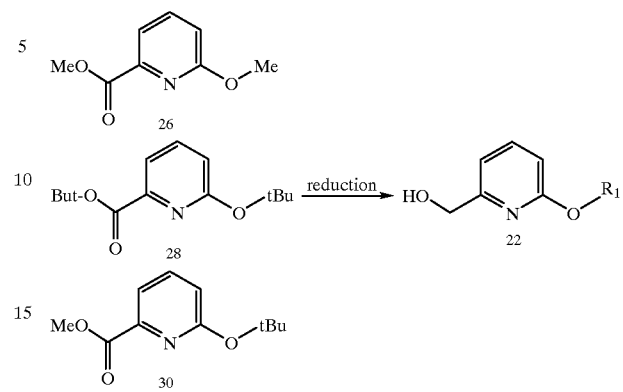

If X and L of different identities are desired, intermediate dianion of formula 24 is reacted with about 1 equivalent of a first electrophile to establish X followed by about 1 or more equivalents of a second electrophile to establish L. Suitable electrophiles include but are not limited to, halogenating agents, such as dibromoethane, hexachloroethane, or a halogen in pure form, such as $Br_2$ or $I_2$; sulfonyl halides; methanesulfonic anhydride; triflic anhydride; carbonates; and haloformates. Preferably, the first electrophile is iodine or 1,2-dibromoethane to establish leaving group X as an iodo- or bromo-group and the second electrophile is tosyl chloride, methanesulfonic anhydride, or triflic anhydride to establish L as the corresponding sulfonyloxy group. (see March, J. *Advanced Organic Chemistry; Reactions Mechanisms, and Structure,* 4th ed., 1992, p. 606–608, Figuly et al, *J. Am. Chem. soc.* 111, 654, (1989); Block et al., *J. Am. Chem. Soc* 111, 658 (1989); Smith et al., *J. Am. Chem. soc.* 111, 665, (1989); and Snieckus et al., *Chem. Rev.* 90, 879–933 (1990), and Uemura et al., *Chem. Lett.* 1195 (1975), all incorporated by reference herein).

A compound of formula 18, wherein L and X are substituted sulfonyloxy groups may also be prepared by quenching dianion of formula 24 with oxygen (to form a phenolate anion) followed by 2 equivalents of sulfonylating agent (e.g., see March, J. *Advanced Organic Chemistry; Reactions Mechanisms, and Structure,* 4th ed., 1992, p. 611 and Parker et al *J. Org. Chem.* 52, 674, (1987), both of which are incorporated by reference herein).

As shown in Scheme VI below, compound of formula 22 may be obtained by standard reduction of any one of a compound of formulas 26, 28, or 30 below. A wide variety of synthetic procedures are available for reduction of such esters to alcohols. (e.g., see M. Hudlicky, Reductions in Organic Chemistry, 2nd ed., 1996 pp 212–217, incorporated by reference herein). Preferably, the reduction is effected with a hydride type reducing agent, more preferably with lithium aluminum hydride.

Compound 26 is known and readily available according to Scheme VII below, wherein methyl picolinate (32) is methoxylated photochemically in an acidic medium. The procedure is described in T. Sugiyama et al., *Tetrahedron Lett.* 4339–4342 (1974) and Takeuchi et al., *Bull. Chem. Soc. Jp.* 47, 1245 (1974), both of which are incorporated by reference herein.

SCHEME VII

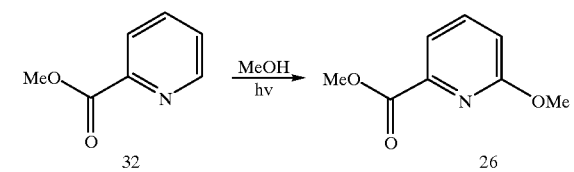

Scheme VIII below describes another method for preparation of compound 26. In the first step 6-hydroxypicolinic acid (34, commercially available, e.g., Aldrich Chemical Co.) is treated with phosphorus pentachloride, phosphoryl chloride, or a similar reagent to simultaneously effect acid chloride formation and nucleophilic displacement of the 2-hydroxyl by chloride (R. M. Acheson, *An Introduction to the Chemistry of Heterocyclic Compounds,* third edition; John Wiley & Sons, 1976 p. 254 and March, J. *Advanced Organic Chemistry; Reactions Mechanisms, and Structure,* 4th ed., 1992, pp. 431–433, both incorporated by reference herein). Other procedures are described in G. Elion et al., *J. Am. Chem. Soc.* 78, 3508 (1956) and J. Davoll et al., *J. Am. Chem. Soc.* 73, 3508 (1951); both of which are incorporated by reference herein.

In the second step of Scheme VIII, the resulting acid chloride 36 is then esterified with methanol followed by chloride displacement with methoxide to form 26.

SCHEME VIII

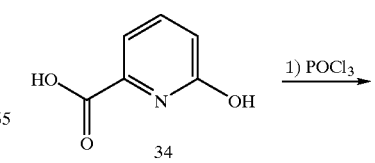

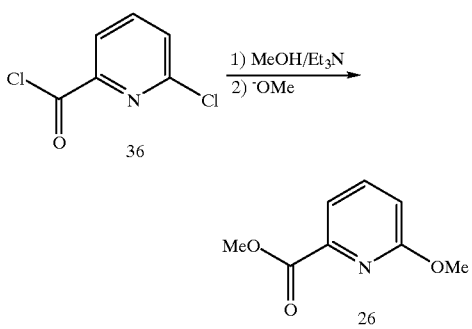

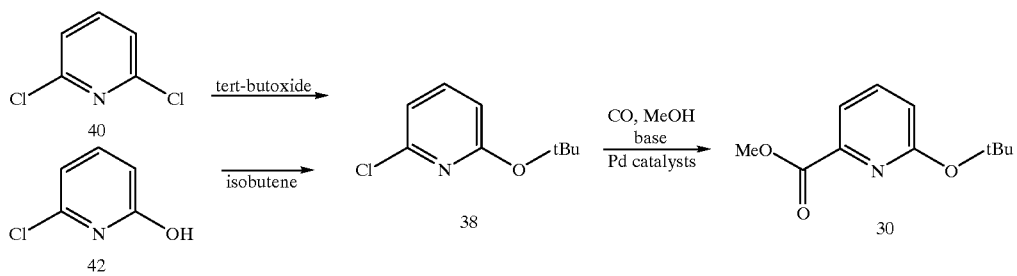

SCHEME X

Such acid catalyzed etherification of phenols is well known in the art, e.g., see March, J. *Advanced Organic Chemistry; Reactions Mechanisms, and Structure*, 4th ed., 1992, p. 763–765.

Ester 30 can be prepared as shown in Scheme X, below. In the first step, compound 38 is available from either of compounds 40 or 42. Carbonylation of 38 then gives 30.

Nucleophilic displacement of chloride from 36 with methoxide is accomplished according to known methods (e.g., see Fyfe, in Patai *The Chemistry of the Hydroxyl Group*, pt. 1: Wily: New York, 1971, pp. 83–124; G. Illuminati *Nucleophilic Heteroaromatic Substitution* in *Adv. Heterocyclic. Chem.* 3, p. 285; and Liveris, M et al., *J. Chem. Soc.* 3486 (1963); all of which are incorporated herein by reference). Compound 26 can also be prepared directly from 34 by treatment with at least two equivalents of an active methylating agent (e.g., with silver carbonate and methyl iodide Kleinberg *Chem. Rev.* 40, 381 (1947 and Bunce et al., *Can. J. Chem.* 54, 2612 (1976)) or diazomethane March, J. *Advanced Organic Chemistry; Reactions Mechanisms, and Structure*, 4th ed., 1992, pp. 388–389, all of which are incorporated by reference herein).

Synthesis of intermediate 28, by simultaneous esterification and etherification of 34 with isobutene and acid, is outlined in Scheme IX.

SCHEME IX

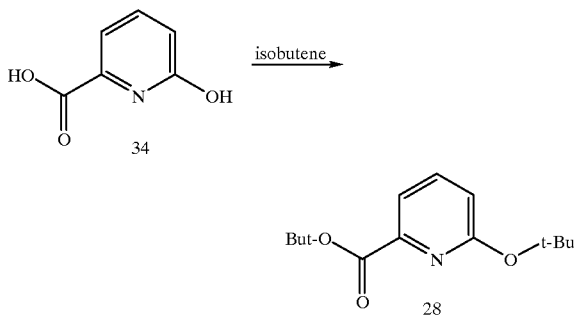

Conversion of 2,6-dichoropyridine (40, commercially available) to 38 may be accomplished by reaction with tert-butoxide. Nucleophilic displacement of halide with alkoxide from halo-pyridines such as 40 are well known in the art (e.g., see Fyfe, in Patai *The Chemistry of the Hydroxyl Group*, pt. 1: Wily: new York, 1971, pp. 83–124; G. Illuminati *Nucleophilic Heteroaromatic Substitution* in *Adv. Heterocyclic. Chem.* 285; and Liveris, M et al., *J. Chem. Soc.*, 3486 (1963), all of which are incorporated herein by reference).

Acid-catalyzed etherification of 6-chloro-2-pyridinol 42 with isobutene also gives compound 38. Acid catalyzed etherification of phenols is also well known in the art, e.g., see March, J. *Advanced Organic Chemistry; Reactions Mechanisms, and Structure*, 4th ed., 1992, p. 763–765.

In the second step of Scheme X above, carbonylation of chloropyridine 38 by treatment with carbon monoxide and base in a solution of methanol in the presence of a palladium catalysts gives 30. Carbonylation of aryl halides has been reviewed in Weil et al., *Organic Synthesis via metal Carbonyls*, vol. 2, 1977, pp. 517 to 543 see also March, J. *Advanced Organic Chemistry; Reactions Mechanisms, and Structure*, 4th ed., 1992, p. 664–665, both of which are incorporated herein by reference. Suitable procedures can be found in Ben-David et al., *J. Am. Chem. Soc.* 111, 8742 (1989); Cacchi et al., *Tetrahedron Lett.* 27, 3931 (1986); Bauld *Tetrahedon Lett.* 1841 (1963); Corey et al., *J. Am. Chem. Soc.* 91, 1233 (1969), Nakayama et al., *Bull. Chem. Soc. Jpn.* 44, 508 (1971), all of which citations are incorporated by reference herein.

While the use of methyl and tert-butyl esters and ethers in intermediates 26, 28, and 30 is an obvious choice in the above preparations, it should be noted that the Schemes are amenable to the production of other esters and ethers as well, and such compounds may be preferred over those shown if they exhibit improved properties from a practical point of view, such as better crystallinity, easier separation from by-products, higher yields, increased stability.

A compound of formula 16 can be prepared as outlined in Scheme XI below.

SCHEME XI

A compound of formula 16, wherein Y is nitro, may be prepared by nitration of 4-methylenecyclohexanone (44) with a strong base (e.g., t-butoxide, potassium hydride, and sodium amide). Compound 44 is well known and has been prepared in various ways (D. Coughlin et al., J. *Org. Chem.* 22 3784–3790 (1979) and references quoted therein). For a discussion of and procedures for α-nitration of ketones see Larson, in Feuer *The Chemistry of the Nitro and Nitroso groups,* Vol 1 (1969) pp.310–316; March, J. *Advanced Organic Chemistry; Reactions Mechanisms, and Structure,* 4th ed., 1992, p. 711, Sheperd et al., J. *Am. Chem. Soc.* 78, 4364 (1956); Feuer et al, J. *Org. Chem.* 37, 2662 (1972); Christensen *Tetrahedron* 25, 181 (1969); Pfeffer et al, *Tetrahedron Lett.* 699 (1970); Feuer et al., J. *Org. Chem.* 41, 2981 (1976); and Feuer et al., J. *Org. Chem.* 43, 4676 (1978), all of which are incorporated herein by reference.

A compound of formula 16, wherein Y is —CHO, may be prepared by reaction of 44 with esters of formic acid and a strong base. For example see, March, J. *Advanced Organic Chemistry; Reactions Mechanisms, and Structure,* 4th ed., 1992, p. 493 and Popik et al., J. *Org. Chem. USSR* 25, 1636 (1989), incorporated by reference herein.

A compound of formula 16, wherein Y is —CN, may be prepared by reaction of 44 with tosyl cyanide (Kahne et al., *Tetrahedron Lett.* 22, 5011 (1981)) or of a derived enamine with an aryl cyanate, for example phenylcyanate (Buttke et al., *Syn. Commun.* 24, 3241 (1994); both of which are incorporated by reference herein).

A compound of formula 16, wherein Y is —N$_3$, may be prepared by α-bromination (Y is —Br) of 44 followed by bromide displacement with azide. Ketone α-bromination is a well known reaction that may be accomplished with a variety of reagents (March, J. *Advanced Organic Chemistry; Reactions Mechanisms, and Structure,* 4th ed., 1992, p. 587 and Larock *Comprehensive Organic Transformations;* VCH: New York, 1989, pp. 369–372, incorporated by reference herein). For example, by first preparing the trimethylsilylenol-ether of 44 followed by reaction with an electrophilic bromine source (J. *Org. Chem.* 39, 1785 (1974) and *Synthesis* 194 (1976), incorporated by reference herein). Displacement of bromide with azide may be accomplished by classical procedures well known in the art (e.g., *Chem. Rev.,* 88, 297 (1988) and *Synthesis* 823 (1979); incorporated by reference herein).

A compound of formula 2 may be transformed into huperzine A (1). For example, when Y is nitro the transformation may be performed according to the a sequence of reaction steps shown in Scheme XII below comprising: (a) reduction of the nitro group to an amino group; (b) protection of the amino group; (c) introduction of an ethylidene appendage at the carbonyl group via a Wittig reaction; (d) C11–C12 olefin isomerization from the predominantly Z-isomer to the predominantly E-isomer; (e) deprotection of the amino and pyridone functions; and (f) C16–C15 to C15–C8 double bond rearrangement.

SCHEME XII

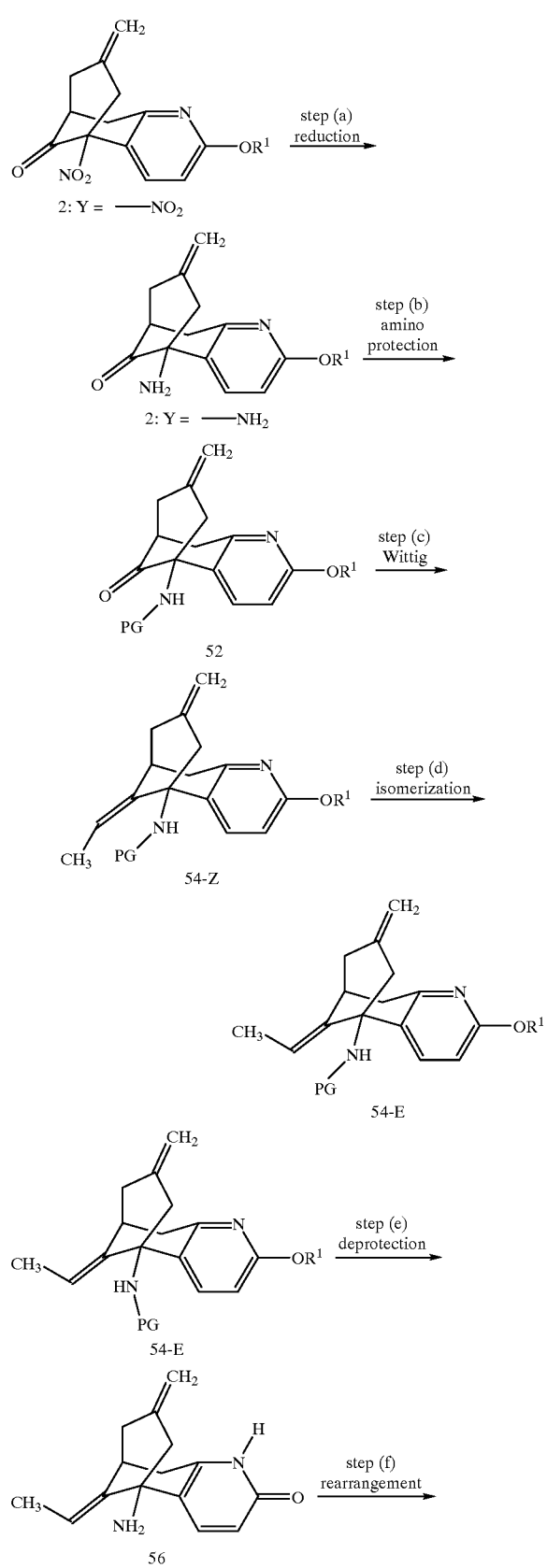

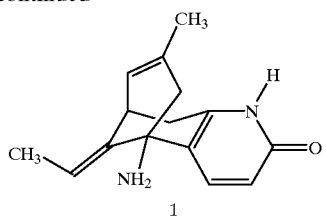

In step (a) of Scheme XII, a compound of formula 2 may be reduced to amine with a variety of reagents (see March, J. *Advanced Organic Chemistry; Reactions Mechanisms, and Structure*, 4th ed., 1992, p. 1216–1217, incorporated herein by reference). Examples of suitable reducing agents include but are not limited to zinc (e.g., *Tetrahedron Lett.* 28, 577 (1987)), tin (e.g., *Org. Syn. Coll.* Vol. 2, 617 (1943)) (for a review of zinc and tin reductions of nitro compounds see; Ioffe et al., *Russ. Chem. Rev.* 35, 19–32 (1966)); titanium trichloride (Ho et al., *Synthesis* 74, 45 (1974)); aluminum-nickel dichloride-tetrahydrofuran (Sarmah et al., *Tetrahedron Lett.* 31, 4065 (1990)); sulfides (Porter *Org. Reac.* 20, 455–481 (1973)); sodium borohydride in conjunction with various catalysts, e.g., nickel dichloride and cobalt dichloride (Jardine et al., *Chem. Commun.* 626 (1970)); aluminum amalgam (Senkus, M. *Ind. Eng. Chem.* 40, 506 (1948); and iron (e.g., J. *Am. Chem. Soc.* 73, 1293(1951) and Calder, A. et al., *Org. Synth.* 52, 77 (1972)). A preferred reducing agent is zinc and hydrochloric acid. All of the above references concerning nitro group reduction are incorporated herein by reference.

In step (b) of Scheme XII above, amino protection of a compound of formula 2 wherein Y is —NH$_2$, is readily accomplished with a variety of protecting groups. Preferably, the amino function is protected as the carbamate. The preferred carbamate is the N-tert-butyloxycarbonyl (N-BOC) group, Carpino, L. A. *Acc. Chem. Res.* 6, 191 (1973), incorporated herein by reference. Preferred reagents for introduction of a BOC group are 2-(tert-butoxycarbonyloximino)-2-phenylacetonitrile (*Tetrahedron Lett.* 4393 (1975) and Itoh, M. et al., *Bull. Chem. Soc. Jpn.* 50 718 (1977)), di-tert-butyl dicarbonate (Tarbell, D. S. et al., *Proc. Natl. Acad. Sci., USA* 69, 730 (1972), and *Synthesis* 223 (1987)); all incorporated by reference herein.

In step (c), introduction of an ethylidene appendage to a compound of formula 52 is preferably accomplished by Wittig olefination to give a compound of formula 54-Z (E/Z about 10/90), see Kaneko, S. et al., *Synlett* 447–448 (1997) and Kozikowski, A. P. et al., *J. Am. Chem. Soc.* 118, 11357–11362(1996), both of which are incorporated herein by reference.

According to step (d), a compound of formula 54-Z may be isomerized from the predominantly Z olefin (E/Z about 10/90) to the predominantly E olefin of formula 54-E ( E/Z about 95/5) with thiophenol/2,2'-azobisisobutyronitrile (AIBN) according to the procedure described in Kaneko, S. et al., *Synlett* 447–448 and Kozikowski, A. P. et al., *J. Am. Chem. Soc.* 118, 11357–11362 (1996); incorporated by reference herein.

Alternatively, as shown in Scheme XIII below, a compound of formula 54-E may be prepared directly from a compound of formula 52 (i.e., steps (c) and (d)). This is accomplished by a protocol described in the literature and recently used in the synthesis of a huperzine A analogue. This procedure comprises reaction of a compound of formula 52 with lithiated 5-phenyl thiopropionate (forms a spiro-β-lactone intermediate) and subsequent thermal or surface-catalyzed [2+2]-cycloreversion of the β-lactone ring, (Kozikowski et al., *J. Chem. Soc., Perkin Trans.* 1, 1287–1297, 1995 and Kozikowski et al., J. Chem. Soc., Perkin Trans. 1, 283–285, 1995, incorporated herein by reference).

SCHEME XIII

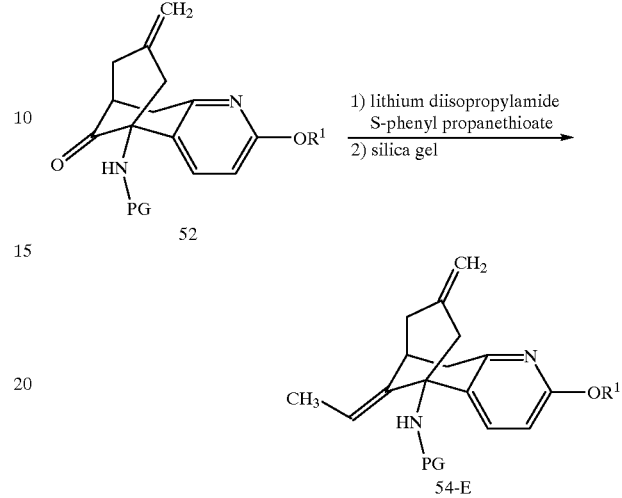

As further shown in step (e) of Scheme XII above, a compound of formula 54-E may be converted to a compound of formula 56 by standard deprotection of the amino- and pyridone-groups. Depending on the protecting group, one of ordinary skill in art will know how to choose the appropriate Step (e) deprotection conditions. When the protecting group is a tert-butyl carbamate, deprotection may be accomplished with trifluoroacetic acid or HCl in an organic solvent. But with other carbamates, deprotection of a compound of formula 54-E to a compound of formula 56 may be accomplished by treatment with aqueous potassium hydroxide in ethylene glycol (Wenkert et al., *J. Am. Chem. Soc.*, 100, 4893 (1978)), potassium hydroxide in aqueous methanol (Natsume et al., *Tetrahedron Lett.* 3477 (1979)), or other bases, such as lithium propylsulfide (Corey et al., J. *Am. chem. Soc.* 100, 2196 (1978)). All of which references concering conversion of a compound of formula 52 to a compound of formula 54-E are incorporated by reference herein.

Step (f) comprises acid catalyzed $C^{16}$–$C^{15}$ to $C^{15}$–$C^8$ double bond rearrangement to provide huperzine A (1). This rearrangement can be accomplished by treatment of a compound of formula 56 with an acid in an organic solvent. For example, heating with trifluoromethansulfonic acid in dry dioxane (Kozikowski et al., *J. Chem. Soc., Perkin Trans.* 1, 1287–1297, (1995)).

In a preferred procedure, outlined in Scheme XIV below (Kozikowski el al., *J. Chem. Soc., Perkin Trans.* 1, 1287–1297, (1996), incorporated herein by reference) a compound of formula 54-E is converted directly to 1 (Steps (e) and (f)) with iodotrimethylsilane wherein the acid generated in this procedure or a subsequent treatment with triflic acid, isomerizes the exocyclic $C^{16}$–$C^{15}$ double bond into the required 15,8-position, thus completing the synthesis of huperzine A (1).

SCHEME XIV

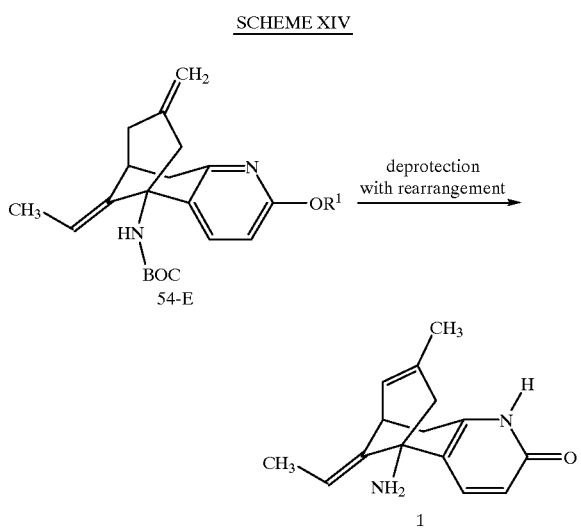

A compound of formula 2, wherein Y is —CHO may be converted to a compound of formula 2, wherein Y is —NH₂ according to the a sequence of reaction steps shown in Scheme XV below. A compound of formula 2, wherein Y is —NH₂ may then be converted into huperzine A as taught in Scheme XIII and XIV above.

SCHEME XV

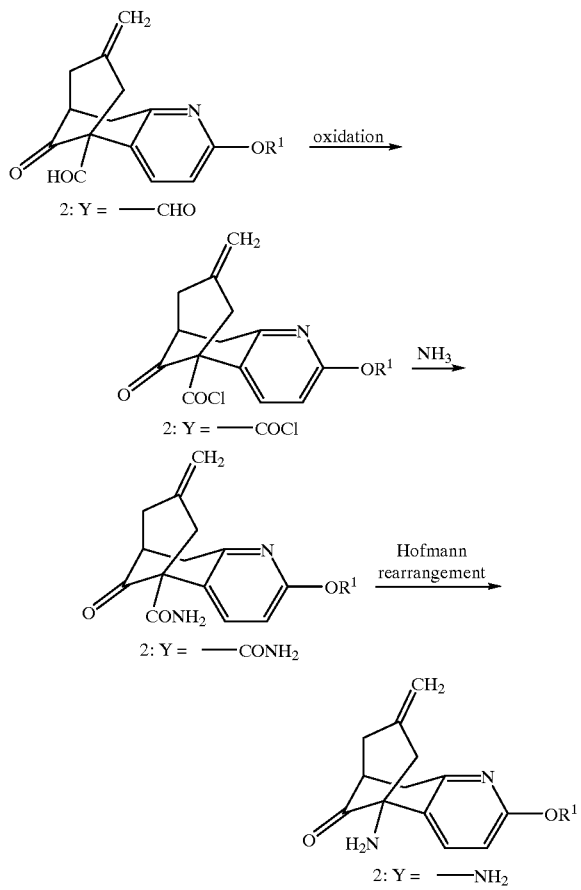

In the first step of Scheme XV, a compound of formula 2, wherein Y is —CHO is converted into a compound of formula 2, wherein Y is —COCl via oxidation with tert-butyl hypochlorite or sulfonyl dichloride ((see March, J. *Advanced Organic Chemistry; Reactions Mechanisms, and Structure*, 4th ed., 1992, p. 697; Wilson et al., *J. Org. Chem.* 47, 1360 (1982); Waling et al., *J. Am. Chem. Soc.* 89, 1515 (1967); Arai *Bull. Chem. Soc. Jpn.* 37, 1280 (1964); and Arai *Bull. Chem. Soc. Jpn.* 38, 252 (1965); all of which are incorporated herein by reference). A compound of formula 2, wherein Y is —COCl may be converted to a compound of formula 2, wherein Y is —CONH₂ via ammonolysis ((see March, J. *Advanced Organic Chemistry; Reactions Mechanisms, and Structure*, 4th ed., 1992, pp. 417–418 and Beckwith in Zabicky *The Chemistry of Amides;* Wiley: New York, 1970, pp. 73–185, both of which are incorporated herein by reference).

A compound of formula 2, wherein Y is —CONH₂ may then be transformed into a compound of formula 2, wherein Y is —NH₂ via the well known Hofmann rearrangement (Wallis *Org. React.* 3, 267–306 (1949); Shioiri *Comp. Org. Syn.* 6, 800–806 (1991); and Synthesis 290 (1974); all three of which are incorporated herein by reference).

A compound of formula 2, wherein Y is —CHO may also be converted to a compound of formula 2, wherein Y is —CONH₂ according to the a sequence of reaction steps shown in Scheme XVI below.

SCHEME XVI

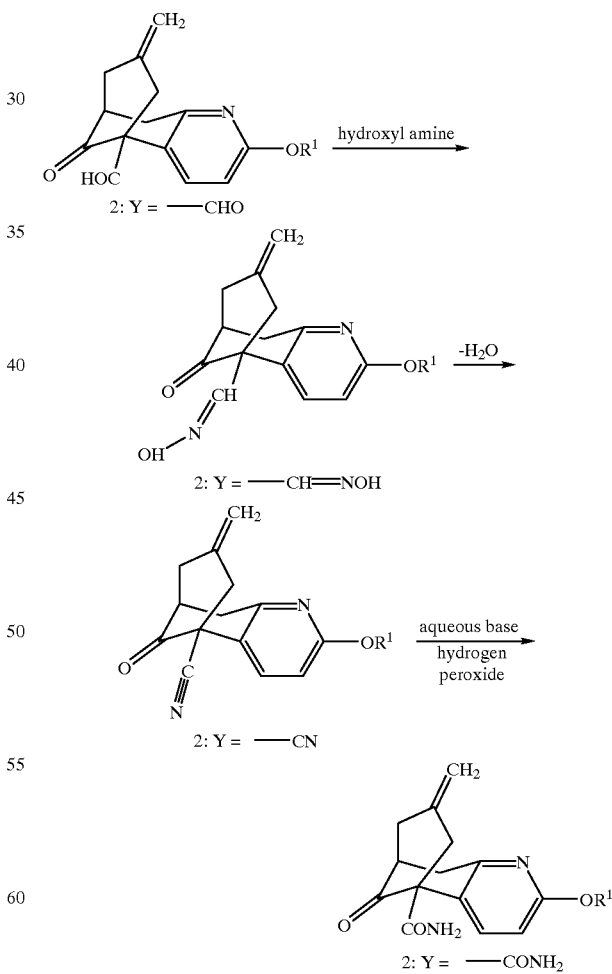

In the first step of Scheme XVI above, a compound of formula 2, wherein Y is —CHO is converted into a compound of formula 2, wherein Y is —CH=NOH via oximation with hydroxylamine. The reaction is well known to those of ordinary skill in the art and can be accomplished by a variety of procedures. For example see, (see March, J. *Advanced Organic Chemistry; Reactions Mechanisms, and Structure,* 4th ed., 1992, pp. 906–907, incorporated herein by reference). A compound of formula 2, wherein Y is —CH=NOH may be converted to a compound of formula 2, wherein Y is —CN, via dehydration. Dehydration of aldoximes to give nitrites is a well known transformation (see March, J. *Advanced Organic Chemistry; Reactions Mechanisms, and Structure,* 4th ed., 1992, pp. 1038–1039 and Friedrich, in Patai; Rappoport, *The Chemistry of Functional groups, Supplement C,* Pt. 2; Wiley: New York, 1978 pp. 1045–1390; and Molina et al., *Synthesis* 1016 (1982); all incorporated herein by reference).

In a more preferred procedure, compound of formula 2, wherein Y is —CHO may be directly converted to a compound of formula 2, wherein Y is —CN in a one step process as disclosed in March, J. *Advanced Organic Chemistry; Reactions Mechanisms, and Structure,* 4th ed., 1992, pp. 907–908 and Olah et al., *Synthesis* 112 (1979), both of which are incorporated herein by reference.

In the last step of Scheme XVI, a compound of formula 2, wherein Y is —CN may be converted to a compound of formula 2, wherein Y is —NH$_2$ by methods well known in the art e.g., see March, J. *Advanced Organic Chemistry; Reactions Mechanisms, and Structure,* 4th ed., 1992, pp. 887–888. A preferred reagent is hydrogen peroxide and hydroxide anion (Cacchi et al., *Synthesis* 243, (1980)).

Alternatively, a compound of formula 2, wherein Y is —CN may be converted to compound of formula 2, wherein Y is —CONH$_2$ via the sequence shown in Scheme XVII. First, a compound of formula 2, wherein Y is —C(S)NH$_2$ is formed by treating a compound of formula 2, wherein Y is —CN with H$_2$S (e.g., Kindler *Liebigs Ann. Chem.* 431, 187 (1923), incorporated herein by reference). Oxidation of the resulting thioamide intermediate then gives the desired product (e.g., with 3-chloroperoxybenzoic acid, Kochlar et al., *Tetrahedron Lett.* 24, 1323 (1983), incorporated herein be reference).

SCHEME XVII

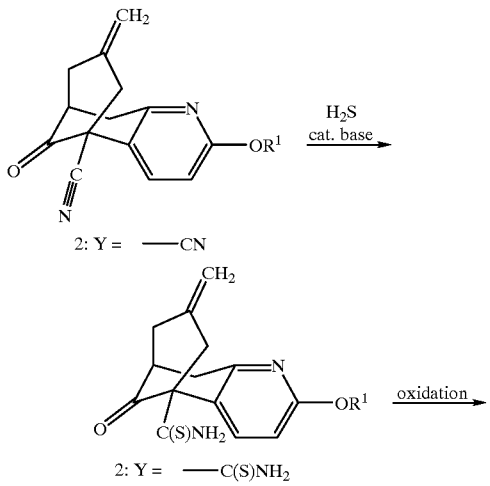

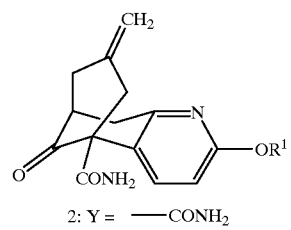

A compound of formula 2, wherein Y is —N$_3$ may be converted to a compound of formula 2, wherein Y is —NH$_2$ by a simple reduction step as shown in Scheme XVIII below. As already discussed, a compound of formula 2, wherein Y is —NH$_2$ may then be converted into huperzine A as outlined in Scheme XIII and XIV above.

The reduction may be effected with a variety of reagents. For example, see Larock *Comprehensive Organic Transformations;* VCH: New York, 1989, pp. 409–410, incorporated by reference herein). Zinc in acetic acid is the reagent of choice (J. *Chem. Soc. Section C: Organic* 414 (1971); incorporated by reference herein).

SCHEME XVIII

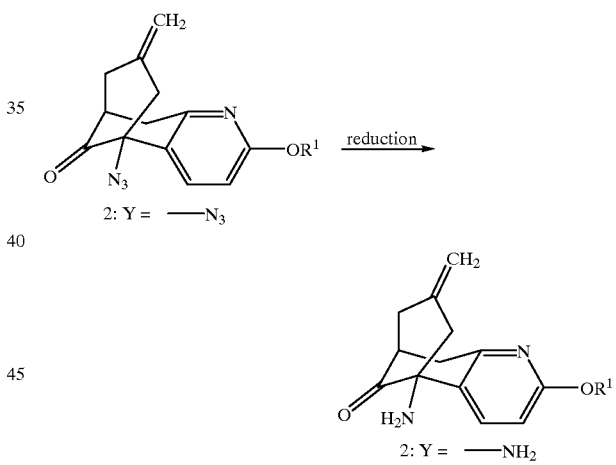

Of course, as is readily apparent to one of skill in the art, the chemistry discussed in Schemes XII–XVIII useful for conversion of a compound of formula 2 to huperzine A can be used as appropriate for conversion of a compound of formula 5 to huperzine A.

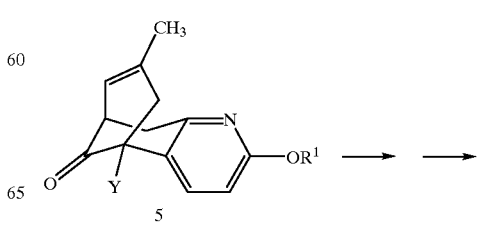

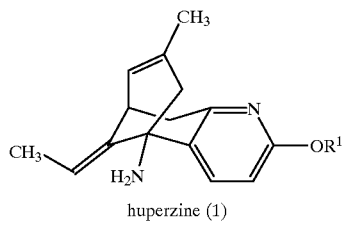

huperzine (1)

Although the invention has been described in considerable detail with reference to certain preferred embodiments, other embodiments are possible. Therefore, the spirit and scope of the appended claims should not be limited to the description of the preferred embodiments contained herein.

The following examples are set forth to assist in understanding the invention and should not, of course, be construed as specifically limiting the invention described and claimed herein. Such variations of the inventions which would be within the purview of those in the art, including the substitution of all equivalents now known or later developed, including changes in formulation or minor changes in experimental design, are to be considered to fall within the scope of the invention disclosed herein.

EXAMPLES

Example 1

Preparation of a Compound of Formula 2 Wherein Y is —NH, by Reduction of a Compound of Formula 2, Wherein Y is —NO$_2$ A vigorously stirred suspension of a compound of formula 2, wherein Y is —NO$_2$, aqueous hydrochloric acid (12 M, about 2 equivalents), and powdered zinc (about 1–10 equivalents) in ethanol (about 20 to about 30 equivalents) is stirred at a temperature of about room temperature to reflux for about 16 to about 24 hours. The reaction mixture is cooled, filtered, diluted with dichloromethane, washed with water, 10% aqueous sodium bicarbonate, and brine, dried (magnesium sulfate), concentrated, and purified by column chromatography using ethyl acetate in hexane as the eluent. Analysis of the product by mass spectroscopy and $^1$H NMR spectroscopy confirms the identity of a compound of formula 2, wherein Y is —NH$_2$.

Example 2

Protection of a Compound of Formula 2 Wherein Y is —NH$_2$ as the N-tert-butyloxcarbonyl Derivative of Formula 52 Wherein Y is —NHR$^2$ and R$^2$ is Tert-butyloxycarbonyl.

To a stirred, cooled (about 0° C.) mixture of a compound of formula 2 wherein Y is —NH$_2$ (1 equivalent) and 4-dimethylaminopyridine (about 0.1 to about 1 equivalent) in dichloromethane (about 5 to about 10 equivalents) is added a solution of di-tert-butyl dicarbonate (about 1 to about 2 equivalents) at a rate of about 20 to about 40 minutes per 0.05 moles in dichloromethane (about 5 to about 10 equivalents) under an inert atmosphere. The mixture is allowed to warm to room temperature and stir for about 1 to 4 hours and then filtered over silica gel using a mixture of ethyl acetate/hexane as the solvent. The fractions containing a compound of formula 52 wherein Y is —NH(tert-butyloxycarbonyl) are concentrated and dried in vacuo. The structure of the product is confirmed by $^1$H NMR and mass spectroscopy.

Example 3

Wittig Reaction of an N-tert-butyloxcarbonyl Derivative of Formula 52 to Give an Intermediate of Formula 54-Z, Wherein Y is —NHR$^2$ and R$^2$ is Tert-butyloxycarbonyl A solution of n-butyllithium (about 5 to about 6 equivalents, about 2.5 M in hexane) is added drop-wise at a rate of about 20 to about 40 minutes per 0.05 moles to a stirred, room temperature suspension of ethyltriphenylphosphonium bromide (about 5 to about 6 equivalents) in dry tetrahydrofuran (about 200 equivalents). The resulting mixture is stirred, preferably at about room temperature for about 1 to about 2 hours, then cooled, preferably to about 0° C. and a compound of formula 52 wherein Y is —NH(tert-butyloxycarbonyl; about 1 equivalent) in tetrahydrofuran (about 70 equivalents) is added drop-wise to the mixture at a rate of about 20 to about 40 minutes per 0.05 moles. The resulting mixture is allowed to warm to about room temperature, and stirred for about 3 to 5 hours. The reaction is quenched with water, the THF is removed by rotary evaporation, and the aqueous residue is extracted with ethyl acetate. The ethyl acetate extracts are washed with brine, dried (magnesium sulfate), and concentrated. Flash chromatography of the crude residue (ethyl acetate/hexanes) gives an olefin of formula 54-Z, wherein Y is —NH(tert-butyloxycarbonyl) as a 10:90 E/Z-mixture by $^1$HNMR spectroscopy.

Example 4

Double Bond Isomerization of a Compound of Formula 54-Z Wherein Y is —NH(tert-butyloxycarbonyl) to a Compound of Formula 54-E Wherein Y is —NHR$^2$ and R$^2$ is Tert-butyloxycarbonyl A stirred mixture of a compound of formula 54-Z wherein Y is —NH(tert-butyloxycarbonyl) (1 equivalent), 2,2'-azobisisobutyronitrile (about 0.7 equivalents), and thiophenol (about 1.5 equivalents) in toluene (about 21 equivalents) is heated at about 85° C. under nitrogen for about 24 hours. The reaction mixture is concentrated and the residue is diluted with dichloromethane, washed with brine, dried (magnesium sulfate), concentrated, and purified by column chromatography. Analysis of the product by mass spectroscopy and $^1$H NMR spectroscopy reveals olefin of formula 54-E wherein Y is —NH(tert-butyloxycarbonyl) to be comprised of an approximately 80/20 to about 85/15 mixture of the E and Z-alkenes, respectively. A subsequent purification by column chromatography gives the pure (at least 95%) Z-isomer.

Example 5

Direct Conversion of a Compound of Formula 52 to a Compound of Formula 54-E, Wherein Y is —NHR$^2$ and R$^2$ is Tert-butyloxycarbonyl A solution of n-butyl lithium (about 1.6 mol/liter in hexane, about 1 to about 1.5 equivalents) is added at a rate of about 20 to about 40 minutes per 0.05 moles to a stirred, cooled solution (about −10° C. to about 5° C.) of diisopropylamine (about 1 to about 1.6 equivalents) in anhydrous tetrahydrofuran (about 5 to about 10 equivalents). After about 15 minutes, the reaction mixture is cooled to about −80° C. and a solution of S-phenyl propanethioate in anhydrous tetrahydrofuran (about 1 to about 5 equivalents) is added at a rate of about 20 to about 40 minutes per 0.05 moles and stirred for about 1 hour. A solution of compound 52, wherein Y is —NH(tert-butyloxycarbonyl) (about 1 equivalent) is added at a rate of about 20 to about 40 minutes per 0.05 moles and the reaction mixture is allowed to warm to about room temperature. The reaction mixture is partitioned between ethyl acetate and water. The organic layer is washed with 10% aqueous potassium carbonate and brine, dried (magnesium sulfate), and concentrated to the crude spiro-β-lactone.

A suspension of the crude spiro-β-lactone as is prepared above and about an equal weight of 200–400 mesh silica gel in about 10 to about 30 equivalents of anhydrous toluene is refluxed for about 1 to about 4 days. The solvent is removed and the residue is purified by flash chromatography using about ethyl acetate in toluene as the eluent. The fractions containing a compound of formula 54-E, wherein Y is —NH(tert-butyloxycarbonyl) are concentrated and dried in vacuo. The structure of the product is confirmed by $^1$H NMR and mass spectroscopy.

Example 6
Concurrent Deprotection and Double Bond Rearrangement of a Compound of Formula 54-E, Wherein Y is —NHR$^2$ and R$^2$ is Tert-butyloxycarbonyl to Give Huperzine A (1)

Iodotrimethylsilane (about 4 equivalents) is added dropwise at a rate of about 20 to about 40 minutes per 0.05 moles to a solution of a carbamate of formula 52, wherein Y is —NH(tert-butyloxycarbonyl) (1 equivalent) in dry chloroform (about 350 to about 450 equivalents) under an inert atmosphere at room temperature. The solution is then refluxed for about 2 to about 24 hours, preferably for about 4 to about 8 hours. The resulting solution is concentrated, the residue dissolved in methanol (about 250 to about 350 equivalents) and refluxed for about 12 to about 24 hours. The volatiles are removed by evaporation, the residue dissolved in dry dioxane (about 100 to about 200 equivalents) and trifluormethansulfonic acid (about 2 equivalents) is added in one portion and the solution stirred at a temperature of about 80 to about 100° C. for about 18 to about 30 hours, preferably at about 90° C. for about 24 hours. The solvent is removed and the residue partitioned between 10% aqueous sodium bicarbonate and 10% methanol in chloroform. The organic layers are washed with brine, dried (magnesium sulfate) and concentrated. Flash chromatography on silica gel half-saturated with ammonia (3% methanol in chloroform) gives huperzine A (1). The structure of the product is confirmed by $^1$H NMR and mass spectroscopy.

Example 7
Condensation of a Compound of Formula 16 with a Compound of Formula 18 to Give a Compound of Formula 2

Hexamethylphosphoramide (about 4 to about 5 equivalents) is added at a rate of about 5 to about 10 minutes per 0.05 moles to a cooled (about −20° C. to about −40° C.) stirred mixture of lithium diisopropylamide (about 2 to about 3 equivalents) in tetrahydrofuran (about 25 equivalents). After about 15 minutes the mixture is cooled to about −70° C. and about 1 equivalent of a compound of formula 16, wherein Y is —NO$_2$ is added in one portion and the resulting mixture is stirred for about an hour. To this stirred mixture is then added in one portion a compound of formula 18 (about 0.3 to about 3 equivalents), the mixture warmed to about 0° C., and stirred for about 1 to about 6 hours. The reaction mixture is quenched with acetic acid followed by water and partitioned between water and ether. The organic layer is dried (magnesium sulfate), concentrated, and purified by flash chromatography using hexane/ethyl acetate as the eluent. The structure of the product is confirmed by $^1$H NMR and mass spectroscopy.

Example 8
Intra-molecular Cyclization of a Compound of Formula 3 to Give a Compound of Formula 2

A suspension of potassium t-butoxide (about 2 equivalents) in monoglyme (about 20 equivalents) is added at a rate of about 5 to about 10 minutes per 0.05 moles to a stirred solution of compound of formula 3 in monoglyme (about 20 equivalents) and dichlorobis[triphenylphosphine] palladium (about 0.4 equivalents), under nitrogen at room temperature. The resulting mixture is stirred at about 70° C. for about 5 hours. The reaction is quenched by adding 1 N aqueous hydrochloric acid until the pH is acidic (about a pH of 4). The resulting mixture partitioned between water and ether. The organic layer is dried (sodium sulfate), concentrated, and purified by flash chromatography using hexane/dichlormethane as the eluent. The structure of the product is confirmed by $^1$H NMR and mass spectroscopy.

Example 9
Condensation of a Compound of Formula 16 With a Compound of Formula 18 to Give a Compound of Formula 3

Hexamethylphosphoramide (about 4 to about 5 equivalents) is added at a rate of about 5 to about 10 minutes per 0.05 moles to a cooled (about −20° C. to about −40° C.) stirred mixture of lithium diisopropylamide (about 2 equivalents) in tetrahydrofuran (about 25 equivalents). After a period of about 15 minutes the mixture is cooled to about −70° C. and about 1 equivalent of a compound of formula 16 is added in one portion and the resulting mixture is stirred for about an hour. To this stirred mixture is then added a compound of formula 18 (about 1 equivalent) in one portion, the mixture warmed to about 0° C., and stirred for about 2 to about 3 hours. The reaction mixture is then quenched with acetic acid, partitioned between water and ether, the organic layer is dried (magnesium sulfate), concentrated, and purified by chromatography using hexane/ethyl acetate as the eluent. The structure is confirmed by $^1$H NMR and mass spectroscopy.

Example 10
Preparation of a Compound of Formula 18, Wherein X is Iodo and Y is 4-toluenesulfonyloxy About 2 to about 3 equivalents of n-butyl lithium (2.5 molar in hexanes) is added under an inert atmosphere (e.g., nitrogen or argon) at a rate of about 20 to about 40 minutes per 0.05 moles to a stirred solution of compound of formula 22 in dry hexane (about 20 to about 50 equivalents) and N,N,N',N'-tetramethylethylenediamine (about 4 to about 5 equivalents), which solution is maintained at a temperature of about −50° C. The resulting mixture is stirred for about 30 minutes then refluxed for about 30 minutes to about 1 hour. The stirred mixture is cooled to back to about −50° C. and about 1 equivalent of iodine in hexane (about 5 equivalents) is added at a rate of about 20 to about 40 minutes per 0.05 moles under an inert atmosphere. After addition, the mixture was stirred for about 15 minutes at −50° C., allowed to warm to about room temperature, stirred for about 15 minutes, and then cooled back to about −50° C. Next, about 1 equivalent of 4-toluenesulfonyl chloride in hexane (about 5 equivalents) is added at a rate of about 20 to about 40 minutes per 0.05 moles. The mixture is stirred for about 15 minutes and allowed to warm to room temperature and stir for an additional 15 minutes. The reaction mixture is then quenched with 1 N aqueous HCl to a pH of about 4 and partitioned between water and ether. The organic layer is dried (magnesium sulfate), concentrated, and purified by chromatography using hexane/ethyl acetate as the eluent. The structure of compound of formula 18, where X is iodo and Y is 4-toluene sulfonyloxy is confirmed by $^1$H NMR and mass spectroscopy.

Example 11
General Procedure for Reduction of Compounds 26, 28, or 30 to Give a Compound of Formula 22

A solution of the ester (1 equivalent) in ether (about 30 to about 60 equivalents), is added at a rate of about 20 to about 40 minutes per 0.05 moles to a suspension of lithium aluminum hydride (about 0.5 to about 1 equivalent) in ether (about 100 to about 600 equivalents) at a temperature of about −70° C. to about 35° C., preferably, about room temperature. The reaction is carefully quenched with ice-water and acidified with a mineral acid to a pH of about 4, preferably with about 10% aqueous hydrochloric acid. The mixture is partitioned between water and ether. The organic layer is dried (magnesium sulfate), concentrated, and purified by flash chromatography using hexane/ethyl acetate as the eluent. The structure of the product is confirmed by $^1$H NMR and mass spectroscopy.

Example 12
Preparation of a Compound of Formula 16, Wherein Y is —NO$_2$

To a cooled (about 5° C.) stirred solution of lithium diisopropylamide (about 1 equivalent) in ether (about 20 equivalents) under an inert atmosphere is added 1 equivalent of 4-methylenecyclohexanone at a rate of about 20 minutes per 0.05 moles. The solution is stirred for about 30 minutes to about 1 hour, cooled (about −50° C. to about −80° C.) and n-propyl nitrate is rapidly added at a rate of about 5 to about 10 minutes per 0.05 moles. After addition, the mixture is allowed to warm to about 0° C. and poured into an equal volume of water. The ether layer is separated, dried (magnesium sulfate), concentrated, and purified by flash chromatography using hexane/ethyl acetate as the eluent. The structure of compound of formula 16, wherein Y is nitro is confirmed by $^1$H NMR and mass spectroscopy.

What is claimed is:

1. A compound represented by the formula:

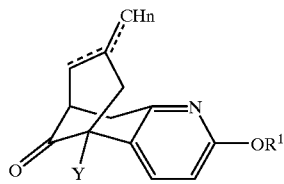

wherein:

$R^1$ is lower alkyl, benzyl, or substituted benzyl;

Y is selected from the group consisting of —NO$_2$, —NHR$^2$, —NR$^3$R$^4$, —CH=NOR$^5$, —COR$^6$, —COCl, —C(O)NR$^6$R$^7$, —CN, —C(S)NR$^6$R$^7$, —N$_3$, —SR$^6$, and —N=CR$^8$R$^9$;

$R^2$ is an amino protecting group;

$R^3$ and $R^4$ are independently selected from the group consisting of —C(O)OR$^{10}$, —C(O)R$^{10}$, allyl, benzyl, substituted benzyl, phenacyl, and 3-acetoxypropyl or $R^3$ and $R^4$ may be taken together to form a cyclic imide;

$R^5$ is selected from the group consisting of hydrogen, lower alkyl, and aryl;

$R^6$ and $R^7$ are independently selected from the group consisting of hydrogen, lower alkyl, substituted lower alkyl, aryl, and substituted aryl or $R^6$ and $R^7$ may be taken together to form a heterocyclic ring;

$R^8$ and $R^9$ are independently selected from the group consisting of hydrogen, lower alkyl, substituted lower alkyl, aryl, and substituted aryl or $R^8$ and $R^9$ may be taken together to form a ring;

$R^{10}$ is selected from the group consisting of lower alkyl, substituted lower alkyl, aryl, substituted aryl, adamantyl, cinnamyl, 2-trimethylsilylethyl, 2-phenylethyl, vinyl, allyl, benzyl, and substituted benzyl; and one broken line is present as a carbon—carbon bond and the other broken line is absent, where the broken line completes an unconjugated carbon—carbon double bond, which double bond is endocyclic whereby n is 3 or the double bond is exocyclic whereby n is 2.

2. The compound according to claim 1, wherein the unconjugated carbon—carbon double bond is exocyclic and n is 2.

3. The compound according to claim 2, wherein Y is selected from the group consisting of —NO$_2$, —CHO, —C(O)NH$_2$, —CH=NOH, —CN, —C(S)NH$_2$, and —N$_3$.

4. The compound of claim 2, wherein $R^2$ is selected from the group consisting of —C(O)OR$^{10}$, —C(O)R$^{10}$, allyl, benzyl, substituted benzyl, lower alkyl, phenacyl, and 3-acetoxypropyl.

5. The compound of claim 2, wherein $R^2$ is —C(O)OR$^{10}$ and $R^{10}$ is lower alkyl.

6. The compound of claim 5, wherein Y is —NO$_2$.

7. A compound represented by the formula:

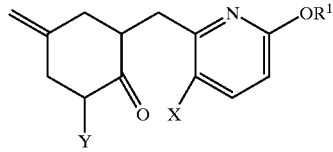

wherein:

$R^1$ is lower alkyl, benzyl, or substituted benzyl;

X is a suitable leaving group;

Y is selected from the group consisting of hydrogen, —NO$_2$, —NR$^3$R$^4$, —CH=NOR$^5$, —COR$^6$, —CO$_2$R$^6$, —C(O)NR$^6$R$^7$, —CN, —C(S)NR$^6$R$^7$, —N$_3$, and —N=CR$^8$R$^9$;

$R^3$ and $R^4$ are independently selected from the group consisting of —C(O)OR$^{10}$, —C(O)R$^{10}$, phenacyl, and 3-acetoxypropyl or $R^3$ and $R^4$ may be taken together to form a cyclic imide;

$R^5$ is selected from the group consisting of hydrogen, lower alkyl, and aryl;

$R^6$ and $R^7$ are independently selected from the group consisting of hydrogen, lower alkyl, substituted lower alkyl, aryl, and substituted aryl or $R^6$ and $R^7$ may be taken together to form a heterocyclic ring;

$R^8$ and $R^9$ are independently selected from the group consisting of hydrogen, lower alkyl, substituted lower alkyl, aryl, and substituted aryl or $R^8$ and $R^9$ may be taken together to form a ring; and $R^{10}$ is selected from the group consisting of lower alkyl, substituted lower alkyl, aryl, substituted aryl, adamantyl, cinnamyl, 2-trimethylsilylethyl, 2-phenylethyl, vinyl, allyl, benzyl, and substituted benzyl.

8. The compound according to claim 7, wherein Y is selected from the group consisting of —NO$_2$, —CHO, —C(O)NH$_2$, —CH=NOH, —CN, —C(S)NH$_2$, and —N$_3$.

9. The compound according to claim 7, wherein X is selected from the group consisting of halo, arylsulfonyloxy, substituted arylsulfonyloxy, alkylsulfonyloxy, substituted alkylsulfonyloxy, phenoxy, substituted phenoxy, and alkylcarbonyloxy.

10. The compound according to claim 7, wherein X is iodo.

11. A method of synthesizing a compound of a formula 3:

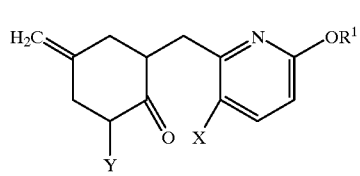

comprising contacting a compound of a formula:

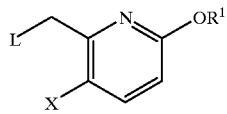

with a compound of a formula:

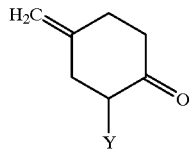

in the presence of a suitable base, to make the compound of formula 3, wherein:

$R^1$ is lower alkyl, benzyl, or substituted benzyl;

Y is selected from the group consisting of —$NO_2$, —$NR^3R^4$, —CH=$NOR^5$, —$COR^6$, —$CO_2R^6$, —C(O)$NR^6R^7$, —CN, —C(S)$NR^6R^7$, —$N_3$, and —N=$CR^8R^9$;

$R^3$ and $R^4$ are independently selected from the group consisting of —C(O)$OR^{10}$, —C(O)$R^{10}$, phenacyl, and 3-acetoxypropyl or $R^3$ and $R^4$ may be taken together to form a cyclic imide;

$R^5$ is selected from the group consisting of hydrogen, alkyl, and aryl;

$R^6$ and $R^7$ are independently selected from the group consisting of hydrogen, alkyl, and aryl or $R^6$ and $R^7$ may be taken together to form a heterocyclic ring;

$R^8$ and $R^9$ are independently selected from the group consisting of hydrogen, alkyl, and aryl or $R^8$ and $R^9$ may be taken together to form a ring;

$R^{10}$ is selected from the group consisting of alkyl, aryl, adamantyl, cinnamyl, 2-trimethylsilylethyl, 2-phenylethyl, vinyl, allyl, and benzyl; and X and L are independently selected from the group consisting of iodo, bromo, chloro, alkylsulfonyloxy, arylsulfonylox, and phenoxy.

12. A method of synthesizing a compound of a formula 2:

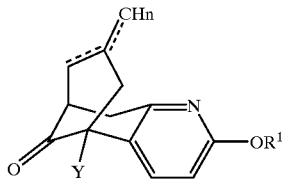

comprising contacting a compound of a formula:

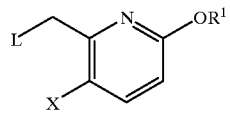

with a compound of a formula:

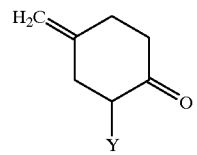

in the presence of a base, to make the compound of formula 2, wherein:

$R^1$ is lower alkyl, benzyl, or substituted benzyl;

Y is selected from the group consisting of —$NO_2$, —$NR^3R^4$, —CH=$NOR^5$, —$COR^6$, —$CO_2R^6$, —C(O)$NR^6R^7$, —CN, —C(S)$NR^6R^7$, —$N_3$, and —N=$CR^8R^9$;

$R^3$ and $R^4$ are independently selected from the group consisting of —C(O)$OR^{10}$, —C(O)$R^{10}$, phenacyl, and 3-acetoxypropyl or $R^3$ and $R^4$ may be taken together to form a cyclic imide;

$R^5$ is selected from the group consisting of hydrogen, alkyl, and aryl;

$R^6$ and $R^7$ are independently selected from the group consisting of hydrogen, alkyl, and aryl or $R^6$ and $R^7$ may be taken together to form a heterocyclic ring;

$R^8$ and $R^9$ are independently selected from the group consisting of hydrogen, alkyl, and aryl or $R^8$ and $R^9$ may be taken together to form a ring;

$R^{10}$ is selected from the group consisting of alkyl, aryl, adamantyl, cinnamyl, 2-trimethylsilylethyl, 2-phenylethyl, vinyl, allyl, and benzyl;

X and L are independently selected from the group consisting of iodo, bromo, chloro, alkylsulfonyloxy, arylsulfonylox, and phenoxy; and one broken line is present as a carbon—carbon bond and the other broken line is absent, where the broken line completes an unconjugated carbon—carbon double bond, which double bond is endocyclic whereby n is 3 or the double bond is exocyclic whereby n is 2.

* * * * *